(12) United States Patent
van Putten et al.

(10) Patent No.: US 10,093,637 B2
(45) Date of Patent: Oct. 9, 2018

(54) PROCESS FOR THE CATALYSED CONVERSION OF PSICOSE INTO 5-HYDROXYMETHYLFURFURAL OR AN ALKYL ETHER THEREOF

(71) Applicant: Furanix Technologies B.V., Amsterdam (NL)

(72) Inventors: Robert-Jan van Putten, Amsterdam (NL); Jan Cornelis van der Waal, Amsterdam (NL); Edserd de Jong, Amsterdam (NL)

(73) Assignee: Furanix Technologies B.V., Amsterdam (NL)

( * ) Notice: Subject to any disclaimer, the term of this patent is extended or adjusted under 35 U.S.C. 154(b) by 51 days.

(21) Appl. No.: 15/120,547

(22) PCT Filed: Mar. 5, 2015

(86) PCT No.: PCT/NL2015/050139
§ 371 (c)(1),
(2) Date: Aug. 22, 2016

(87) PCT Pub. No.: WO2015/133902
PCT Pub. Date: Sep. 11, 2015

(65) Prior Publication Data
US 2017/0008865 A1    Jan. 12, 2017

(30) Foreign Application Priority Data
Mar. 5, 2014 (NL) .................................... 2012365

(51) Int. Cl.
*C07D 307/48* (2006.01)
*C07D 307/46* (2006.01)

(52) U.S. Cl.
CPC ......... *C07D 307/48* (2013.01); *C07D 307/46* (2013.01)

(58) Field of Classification Search
CPC .................................................. C07D 307/48
See application file for complete search history.

(56) References Cited

FOREIGN PATENT DOCUMENTS

| | | |
|---|---|---|
| EP | 1834950 A1 | 9/2007 |
| EP | 2565189 A1 | 12/2007 |
| EP | 2103606 A1 | 9/2009 |
| WO | WO 2012091570 A1 * | 7/2012 ............. C07C 67/00 |

OTHER PUBLICATIONS

U.S. Food and Drug Administration. "Agency Response Letter GRAS Notice No. GRN 000400." (c) Jun. 18, 2012. Available from: <https://www.fda.gov/Food/IngredientsPackagingLabeling/GRAS/NoticeInventory/ucm319617.htm>.*
Guthrie, J., et al. "Food sources of added sweetners in the diets of Americans." J. American Dietetic Association. (Jan. 2000), vol. 100, No. 1, pp. 43-51.*
Sigma Aldrich. "D-(+)-Glucose." © Oct. 7, 2012. Available from: <https://web.archive.org/web/20121007035743/http://www.sigmaaldrich.com/catalog/product/SIGMA/G8270?lang=en&region=>.*
Joseph B. Binder, et al., "Mechanistic Insights on the Conversion of Sugars into 5-hydroxymethylfurfural", The Royal Society of Chemistry, pp. 765-771, May 13, 2010.
Robert-Jan van Putten, et al., "Dehydration of Different Ketoses and Aldoses to 5-Hydroxymethylfurfural", ChemSusChem, 2013.

* cited by examiner

*Primary Examiner* — Noble E Jarrell
*Assistant Examiner* — John S Kenyon
(74) *Attorney, Agent, or Firm* — Hoffmann & Baron, LLP

(57) ABSTRACT

Psicose is converted into 5-hydroxymethylfurfural or an alkyl ether thereof in a process for the catalyzed conversion of psicose, including the steps of: a. forming a feed including psicose and water or at least one alkanol or a mixture thereof and b. converting the psicose in the feed at a temperature in the range of 50 to 300 degrees Celsius in the presence of a catalyst.

11 Claims, No Drawings

PROCESS FOR THE CATALYSED CONVERSION OF PSICOSE INTO 5-HYDROXYMETHYLFURFURAL OR AN ALKYL ETHER THEREOF

CROSS-REFERENCE TO RELATED APPLICATIONS

This application is the National Stage of International Application No. PCT/NL2015/050139 filed Mar. 5, 2015, which claims the benefit of Netherlands Application No. NL 2012365, filed Mar. 5, 2014, the contents of which is incorporated by reference herein.

TECHNICAL FIELD

The current invention concerns a process for the catalysed conversion of psicose into 5-hydroxymethylfurfural (5-HMF) or an alkyl ether thereof.

BACKGROUND ART

Biomass, and in particular sugars therein, are considered an important and sustainable source for building blocks previously made from petrochemical sources. Interest in mono-, di- and polysaccharides is increasing. The resulting 5-HMF may be used as fuel or fuel additive, but also as precursor for a building block in polymers (e.g. polyesters) and the like. For instance, Avantium is currently developing a process for the production of polyethylenefurandicarboxylate (PEF) from $C_6$ sugars as a next generation replacement material for polyethyleneterephthalate (PET).

The conversion of in particular glucose and fructose has been studied in detail. For instance, it is known that fructose is more efficiently converted to 5-HMF than glucose. The conversion is typically conducted with an acidic catalyst, a homogeneous or a heterogeneous catalyst, more preferably a solid catalyst. Also, various solvent systems have been used, e.g., organic solvents, ionic liquids, etc.

Methods for the manufacture of 5-hydroxymethylfurfural and ethers thereof are described in for instance EP2103606 and EP2565189. The hexose-containing starting material is typically fructose or glucose.

More recently saccharides (sugars) other than fructose and glucose have been studied. The reason for this lack of interest in the past is that one would expect no significant differences in reactivity and selectivity between the various saccharides.

In Energy Environ. Sci., 2010, 3, 765-771, "Mechanistic insights on the conversion of sugars into 5-hydroxymethylfurfural", a paper by Binder et al, the transformation of D-mannose and D-galactose into HMF was studied. Also studied was the transformation of lactose and D-tagatose. The reactions were conducted in an ionic liquid, dimethylacetamide (DMA) or dimethyl sulphoxide (DMSO). The investigation revealed that some, but not all hexoses, can be transformed efficiently into HMF. Among others D-psicose, D-tagatose and L-sorbose were studied. In one experiment the yield of HMF from psicose with $H_2SO_4$ in DMSO was higher than the corresponding conversion of sorbose. In many other experiments the yields of HMF from psicose and sorbose were similar. Other experiments provided proof of poor reactivity of tagatose.

The article states that the HMF yield of HMF from psicose with $H_2SO_4$ in DMSO is similar to those obtained with fructose. It concludes that among fructose and its three epimers the highest HMF yields were obtained from fructose and psicose.

In a paper submitted to ChemSusChem, 2013, 6, 1681-1687, "Dehydration of different ketoses and aldoses to 5-hydroxymethylfurfural", by Van Putten et al, a kinetic study on the acid-catalysed dehydration of ketoses and aldoses was reported. Acid-catalyzed dehydration in water with different concentrations of sulphuric acid at various reaction times revealed tagatose to be the more reactive saccharide as compared to sorbose and fructose. Modelling studies indicated that psicose, which was not tested experimentally, would be the least reactive ketose for the dehydration towards HMF.

EP 1834950 discloses a method for the manufacture of ethers of 5-hydroxymethyl furfural by reacting a glucose-containing starting material with an alcohol in the presence of a catalytic or sub-stoichiometric amount of acid catalyst. The process can also be applied to sucrose and be performed in a continuous flow reactor. The patent application does not mention the use of any starting material other than glucose or fructose.

The inventors set out to find monosaccharides that can be converted into 5-HMF in water or the ether derivative thereof in an alcohol, that are better than fructose. This has now been achieved.

SUMMARY OF INVENTION

Accordingly the invention concerns a process for the conversion of psicose into 5-hydroxymethylfurfural or an alkyl ether thereof, comprising the steps of:
 a. forming a feed comprising psicose and water or at least one alkanol or a mixture thereof, and
 b. converting the psicose in the feed at a temperature in the range of 50 to 300 degrees Celsius in the presence of an acid catalyst.

As the prior art teaches that fructose and psicose yield similar 5-HMF yields in aprotic solvents, it is surprising that psicose yields significantly better 5-HMF yields than fructose when the reaction is conducted in water, an alkanol or a mixture thereof.

DETAILED DESCRIPTION OF THE INVENTION

In the ChemSusChem paper mentioned above, psicose was not included in the experimental study. However, it is mentioned in the paper, as psicofuranose, in Figure 7. In this paper the reaction Gibbs free energy ΔG 298K was computed for proposed carbocation intermediates believed to be formed in the rate-determining step for dehydration of ketohexoses toward the formation of 5-HMF. Interestingly, according to these calculations the intermediate for psicose was substantially less favourable than that for tagatose, fructose and sorbose. This would rather indicate that psicose is the least reactive sugar in this group with regard to 5-HMF formation and therefore not a saccharide of interest.

In the paper by Binder et al, page 769, left column, it is mentioned that the yield of 5-HMF from psicose with $H_2SO_4$ in DMSO is higher than that of either tagatose or sorbose and similar to those obtained with fructose. Under other conditions, however, yields of 5-HMF from psicose and sorbose were similar. Especially when another solvent, viz. DMA, was used the yields of 5-HMF from sorbose and psicose were similar. Therefore, the skilled person would not expect that the conversion of psicose would result in higher yields of 5-HMF and ethers thereof than the conversion of fructose when water and/or alkanols would be used as solvent or diluent.

As is known in chemistry, solvents may significantly affect the reaction rate or competing reaction rates if there are more reactions taking place. When considering the conversion of sugars, the final yield may be adversely affected by side-reactions to for instance polymeric compounds (humins) and the known byproducts levulinic acid and its alkyl ester, and hydroxyacetylfuran and its alkyl ether.

Solubility in water is generally not an issue. If solubility in the alkanol is an issue, then water or a co-solvent may be added. The liquid in the feed described above may therefore comprise a co-solvent. Alternatively, the liquid may be composed of water, an alkanol or a mixture of alkanols, or a mixture of one or more alkanols and water. Preferably, the liquid comprises the water and/or the one or more alkanols in a molar ratio versus psicose that is greater than 1. The amount of water and/or alkanol(s) is preferably greater than stoichiometric. More preferably, an amount of water and/or alkanol(s) is used that is sufficient to dissolve the psicose. In this case, the water and/or alkanols act as solvent and alkanols can also act as a reactant. That being said, it is also possible to convert the sugar when it is in the feed in the form of a slurry with a diluent. The solubility of a ketose in an alkanol can be increased by the formation of alkyl glycosides in acid-catalysed acetalisation, as described in a previous patent, e.g. EP2658849. In a preferred embodiment, the psicose is therefore included in the feed in the form of an alkyl glycoside. The acetalisation may be done with a homogeneous catalyst or a heterogeneous catalyst. There is no upper limit to the amount of water and/or alkanol(s). On the other hand, excessively high amounts of liquid in the system may lead to a too dilute reaction mixture, which is not preferred. As mentioned, one or more co-solvents may be added. The co-solvent may aid in the dissolution of the psicose. The co-solvent may be selected from the group consisting of sulfoxides, preferably DMSO; ketones, preferably methyl ethylketone, methylisobutylketone and acetone, or mixtures of two or more of the above co-solvents. The may comprise from 5 to 75, preferably from 10 to 50 percent by volume of co-solvent, the remainder being water and/or one or more alkanols.

The one or more alkanols may be linear or branched. Preferably, the alkanol(s) is/are selected from the group consisting of primary branched or unbranched aliphatic alcohols. For instance, the alkanol(s) may be selected from the group consisting of primary $C_1$-$C_5$ (un)branched aliphatic alcohols, preferably methanol, ethanol, 1-propanol, 2-hydroxymethyl-propanol, or 1-butanol. The more preferred alkanols are methanol and/or ethanol. The resulting ethyl and/or methyl ethers; methoxymethylfurfural (MMF) or ethoxymethylfurfural (EMF), have a high energy content and may directly be used as a fuel additive, e.g. as an alternative for MTBE, or as a fuel by itself. As indicated, mixtures of alkanols may also be employed. Methanol is the most preferred alkanol in the method of the present invention.

The catalyst in the method of the production of HMF and ethers thereof is preferably an acid catalyst. The acid catalyst may be selected from amongst (halogenated) organic acids, inorganic acids, salts, Lewis acids, ion exchange resins and zeolites or combinations and/or mixtures thereof. Preferably, the catalyst is a heterogeneous catalyst. Nonetheless, the catalyst may also be a homogenous catalyst. The acid catalyst may be a protonic, Brønsted acid or, alternatively, a Lewis acid. The acid may be organic or inorganic. For instance, the organic acid may be selected from amongst oxalic acid, levulinic acid, maleic acid, methanesulphonic acid or para-toluenesulphonic acid. The inorganic acid may be selected from the group consisting of phosphoric acid, sulphuric acid, hydrochloric acid, hydrobromic acid, nitric acid, hydroiodic acid, optionally generated in situ, and mixtures thereof. In certain embodiments, the inorganic acid is selected from the group of sulphuric acid, phosphoric acid, hydrochloric acid, nitric acid.

Also a salt may be used. The salt can be one of $(NH_4)_2SO_4/SO_3$, ammonium phosphate, triethylamine phosphate, pyridinium salts, pyridinium phosphate, pyridinium hydrochloride/hydrobromide/perbromate, dimethylaminopyridine (DMAP), aluminium salts, Th and Zr ions, zirconium phosphate, Cr-, Al-, Ti-, Ca-, In-ions, $ZrOCl_2$, $VO(SO_4)_2$, $TiO_2$, V-porphyrine, Zr-, Cr-, Ti-porphyrine. The Lewis acid can be one of $ZnCl_2$, $AlCl_3$, $BF_3$.

The ion exchange resins may be one of Amberlyst, Amberlite, Diaion, Lewatit (trademarks). It is preferred that the acid catalyst is a solid catalyst selected from the group consisting of acid resins, natural clay minerals, zeolites, supported acids such as silica impregnated with mineral acids, heat treated charcoal, metal oxides, metal sulfides, metal salts and mixed oxides and mixtures thereof. Also mixtures or combinations of the acid catalysts described above may be used.

The temperature at which the reaction is performed may vary. In general it is preferred that the reaction is carried out at a temperature from 50 to 300 degrees Celsius, preferably from 125 to 250, more preferably from 175 to 225 degrees Celsius. Temperatures higher than 300 degrees Celsius are less preferred as many by-products may occur. Performing the reaction below the lowest temperature is also less preferable because of the slow reaction rate.

The psicose-containing starting material can be selected from a wide variety of feeds. In general any feed with a sufficiently high psicose content can be used. Suitably, the psicose-containing starting material comprises at least 25% wt, preferably at least 50% wt and more preferably at least 75% wt of psicose, based on the weight of the starting material.

The catalyst can be added to psicose dissolved in a liquid in an amount varying from 0.01 to 40 mole % drawn on the psicose (e.g., sugar content of the psicose-containing starting material). It is preferably added in an amount from 0.1 to 30 mole %, more preferably from 1 to 20 mole %.

The method of the current invention may be carried out in a batch process or in a continuous process, and with or without recycle of at least part of the product stream to control the reaction temperature. In such a case the recycle may be effected via a heat exchanger. For instance, the method of the invention can be performed in a continuous flow process. In such a process, homogenous catalysts may be used and the residence time of the reactants in the flow process is between 0.1 second and 10 hours, preferably from 1 second to 5 hours, more preferably from 1 minute to 1 hour.

Alternatively, the continuous flow process may be a fixed bed continuous flow process, e.g. a reactive catalytic distillation process, with preferably a heterogeneous acid catalyst. To initiate or regenerate the heterogeneous acid catalyst or to improve performance, an inorganic or organic acid may be added to the feed of the fixed bed or reactive distillation continuous flow process. In a fixed bed process, the liquid hourly space velocity (LHSV) can be from 1 to 1000, preferably from 5 to 500, more preferably from 10 to 250 and most preferably from 25 to 100 $hr^{-1}$.

As indicated, the 5-hydroxymethylfurfural or alkyl ether thereof may be used e.g. as fuel or fuel additive, as precursor for fuel or fuel additives, or as a starting material for useful chemical compounds. Thus, they may be the precursor to monomers for use in biobased polymers.

Examples are enclosed below to illustrate the process of the current invention.

The examples are not meant to limit the scope of the invention.

EXPERIMENTS

Example 1

65 mg/ml substrate was reacted in pure methanol at 100 degrees Celsius in the presence of 17 mM $H_2SO_4$. A batch setup with 2000 kPa (20 bar) nitrogen overpressure was used. Results were measured after a reaction time of 150 min. percentages are molar percentages, based on the initial number of moles of the substrate.

The sugars and reaction products were quantified with the aid of ultra performance liquid chromatography (UPLC) analysis with an internal standard (saccharine, Sigma Aldrich). In the conversion results the formed methylated sugars are measured as unconverted sugar, since it is known from EP2658849 that methyl fructosides are a suitable feed for HMF and MMF production. A Waters Acquity UPLC chromatograph, equipped with a Waters Acquity UPLC HSS C18, 2.1×100 mm, 1.8 μm column and with UV and evaporative light scattering (ELS) detectors, was used. The UV detector was used to measure HMF, MMF and hydroxyacetylfuran (HAF) (230 nm) and saccharine (250 nm) and the ELS detector was used to measure all sugars and saccharine. A gradient elution at a constant flow of 0.4 ml/min at a temperature of 50 degrees Celsius was used according to the following scheme:

Eluent A: 0.2% trifluoroacetic acid in water;
Eluent B: acetonitrile/methanol 1:1 v/v.
Binary Pump Program

| Time (min) | Eluent A (%) | Eluent B (%) | Flow (ml/min) |
|---|---|---|---|
| Initial | 98.0 | 2.0 | 0.40 |
| 4 | 90.0 | 10.0 | 0.40 |
| 10 | 85.0 | 15.0 | 0.40 |
| 12 | 44.0 | 56.0 | 0.40 |
| 13 | 2.0 | 98.0 | 0.40 |
| 14 | 2.0 | 98.0 | 0.40 |
| 15 | 98.0 | 2.0 | 0.40 |
| 16 | 98.0 | 2.0 | 0.40 |

ELSD Settings

| Detector | Gain | 250 |
|---|---|---|
|  | Time constant | Normal |
| Gas pressure | 276 kPa (40 psi) |  |
| Nebulizer mode | Cooling |  |
| Drift tube temperature | 60 degrees Celsius |  |

Methyl levulinate (ML) and levulinic acid (LA) were analyzed on GC with 1,4-dioxane as the internal standard:
Column: VF WAXms, 0.25 mm id film thickness 0.25 μm, 30 m
Detection: FID

| Oven | |
|---|---|
| Initial temperature | 60 degrees Celsius |
| Hold time | 2 min |
| Ramp 1 | 50 degrees Celsius/min |
| End temperature | 250 degrees Celsius |
| Hold time | 2 min |
| Mode | Split |
| Temperature | 250 degrees Celsius |
| Split flow | 200 mL/min |
| Flow mode | Constant flow |
| Flow | 2 mL/min |
| Gas saver flow | 25 mL/min |
| Gas saver time | 25 min |
| Flame | On |
| Base Temperature | 275 degrees Celsius |
| Air | 350 mL/min |
| $H_2$ | 35 mL/min |

For UPLC saccharine was used as standard and for GC 1,4-dioxane was used as a standard. Both were added in stock solution to the reactor after completion of the reaction. Yields of MMF, HMF and ML were always the highest starting from psicose as the substrate. As shown in Table 1, the yields from fructose and tagatose were comparable and the yields from sorbose were always the lowest by far. The yield of HAF was consistently the highest for sorbose (up to 7%). For the other ketoses very small amounts were also observed (in GC, not quantified). Its methyl ether was also observed in small amounts. Apart from ML, also small amounts of LA were observed.

TABLE 1

Yields of relevant products in methanol in the presence of 17 mM sulphuric acid after 150 min at 100 degrees Celsius

| Substrate | Substrate conversion (%) | MMF yield (%) | HMF yield (%) | ML yield (%) |
|---|---|---|---|---|
| D-Psicose | 97.1 | 54.8 | 3.5 | 27.8 |
| D-Tagatose | 93.5 | 42.4 | 3 | 24.6 |
| D-Fructose | 88.3 | 43.8 | 3.6 | 22 |
| L-Sorbose | 83.4 | 26.1 | 1.5 | 15.9 |

Example 2

65 mg/ml substrate was reacted in pure water at 120 degrees Celsius in the presence of 33 mM $H_2SO_4$. A batch setup with 2000 kPa (20 Bar) nitrogen overpressure was used. The reaction times used were 75 min. The same methods for analysis were used as in Example 1. Results are presented in Table 2.

TABLE 2

Yields of relevant products in water in the presence of 33 mM sulphuric acid after 75 min at 120 degrees Celsius

| Substrate | Substrate conversion (%) | HMF yield (%) | LA yield (%) |
|---|---|---|---|
| D-Psicose | 35.7 | 26.8 | 1.5 |
| D-Tagatose | 47.8 | 30.1 | 1.8 |
| D-Fructose | 21.4 | 16.3 | 0.8 |
| L-Sorbose | 19.0 | 11.3 | 0.6 |

Around 2% of hydroxyacetylfuran yield was observed for sorbose, for the other sugars only trace amounts could be found at best. The HMF selectivity, which is calculated by dividing the HMF yield by the substrate conversion, was much better for psicose, at around 75%, than for tagatose, at around 63%. Furthermore the data clearly show that psicose is a better substrate than fructose for HMF production, as it has much higher yield with a comparable selectivity.

The invention claimed is:

1. A process for the catalysed conversion of psicose into 5-hydroxymethylfurfural or an alkyl ether thereof, comprising the steps of:
   a. forming a feed comprising psicose and water and at least one alkanol or a mixture thereof, wherein the at least one alkanol is selected from the group consisting of 2-hydroxymethyl-propanol and 1-butanol, and mixtures thereof; and
   b. converting the psicose in the feed at a temperature in the range of 50 to 300 degrees Celsius in the presence of an acid catalyst.

2. The process of claim 1, wherein the feed comprises water and at least one alkanol, or a mixture thereof in a molar ratio versus the psicose that is greater than 1.

3. The process of claim 1, wherein the feed comprises a co-solvent.

4. The process of claim 1, wherein an amount of water and alkanol or a mixture thereof is used that is sufficient to dissolve the psicose.

5. The process of claim 1, wherein the acid catalyst is selected from organic acids, inorganic acids, salts, Lewis acids, ion exchange resins, zeolites and combinations or mixtures thereof.

6. The process of claim 1, wherein the acid catalyst is a heterogeneous catalyst.

7. The process of claim 1, wherein the acid catalyst is added to the feed in an amount varying from 0.01 to 40 mol % drawn on the psicose.

8. The process of claim 1, wherein the psicose is included in the feed in the form of an alkyl glycoside.

9. The process of claim 8, wherein the alkyl glycoside is formed by reacting psicose in the at least one alkanol in the presence of a homogeneous catalyst.

10. The process of claim 8, wherein the alkyl glycoside is formed by reacting psicose in the at least one alkanol in the presence of a heterogeneous catalyst.

11. The process of claim 1, which is performed in a continuous flow process.

* * * * *